United States Patent [19]
Fogel et al.

[11] Patent Number: 5,506,501
[45] Date of Patent: Apr. 9, 1996

[54] METHOD AND APPARATUS FOR AIDING MACHINE OIL ANALYSIS

[75] Inventors: Anthony G. Fogel, Knoxville, Tenn.; Kenneth W. Brown, Halfway House, South Africa

[73] Assignee: Computational Systems, Inc., Knoxville, Tenn.

[21] Appl. No.: 330,700

[22] Filed: Oct. 28, 1994

[51] Int. Cl.$^6$ ............................................. G01N 33/00
[52] U.S. Cl. ................... 324/204; 73/53.07; 73/64.560; 73/61.71
[58] Field of Search ............... 73/61.75, 61.42, 73/53.07, 53.07, 53.05; 324/204

[56] References Cited

U.S. PATENT DOCUMENTS

| | | | |
|---|---|---|---|
| 1,940,772 | 12/1933 | Schoenberg | 88/14 |
| 2,599,583 | 6/1952 | Robinson et al. | 175/183 |
| 2,889,736 | 6/1959 | Borg | 88/14 |
| 3,049,964 | 8/1962 | Miller et al. | 88/14 |
| 3,371,574 | 3/1968 | Dwyer | 88/14 |
| 3,790,279 | 2/1974 | Skala | 356/70 |
| 3,892,485 | 7/1975 | Merritt et al. | 356/201 |
| 4,003,661 | 1/1977 | Yamano | 356/201 |
| 4,029,554 | 6/1977 | Ellison | 204/1 |
| 4,047,814 | 9/1977 | Westcott | 356/38 |
| 4,302,754 | 11/1981 | Magee et al. | |
| 4,492,461 | 1/1985 | Jones et al. | |
| 4,646,070 | 2/1987 | Yasuhara et al. | 340/603 |
| 4,677,847 | 7/1987 | Sawatari et al. | 73/64 |
| 4,692,698 | 9/1987 | Lewis | 324/204 |
| 4,701,713 | 10/1987 | Eaton et al. | 324/442 |
| 4,741,204 | 5/1988 | Luck et al. | 73/116 |
| 4,791,374 | 12/1988 | Yodice et al. | 324/439 |
| 4,796,204 | 1/1989 | Inoue | 364/550 |
| 4,831,362 | 5/1989 | Tsaprazis | 340/515 |
| 4,857,829 | 8/1989 | Sagae et al. | 324/61 |

FOREIGN PATENT DOCUMENTS

| | | |
|---|---|---|
| 2165650 | 4/1988 | United Kingdom. |
| 2160655 | 5/1989 | United Kingdom. |

OTHER PUBLICATIONS

Brochure entitled: *Tribometrics, Inc. Model 56 Wear Particle Analyzer.*
Paper having the heading of *ICC Federrated.*
Paper having the heading of *Analex.*
Paper having the heading of *Sensys.*
B. J. Roylance & A. L. Price, *The Development of A Computer–Aided Systemic Particle Analysis Procedure–CASPA*, Dec. 1992 Lubrication Engineering, p. 940.

*Primary Examiner*—Hezron E. Williams
*Assistant Examiner*—Jay L. Politzer
*Attorney, Agent, or Firm*—Luedeka, Neely & Graham

[57] ABSTRACT

A method and apparatus is provided to prepare samples of viscous industrial fluids such as machine lubrication oil for analysis for the presence of magnetically responsive particles and other suspended solids. A test sample of the fluid is held in non-magnetic vessel. This sample holding vessel is positioned in the cooperative pocket of a portable, hand-held vibrator and stimulated by 120 to 150 Hz, vibration for a designated period of time, usually 30 to 60 seconds. A strong permanent magnet below the vibrating vessel pocket is oriented to emit a magnetic field on or within the sample simultaneously with the vibrations to induce rapid settlement of any magnetic particles toward the vessel bottom. Such vibration also assists and accelerates pure gravity settlement of non-magnetic particles. Entrained gas bubbles tend to rise more rapidly to the sample surface due to the vibrational stimulation. After a brief vibrational interval within the magnetic flux fields and while the sample vessel remains in the flux field, oil is poured from the vessel across a suitable planar sheet filter to segregate non-magnetic particles originally suspended in the sample. Still within the flux field, the substantially empty vessel is rinsed with a solvent to immobilize residual non-magnetic particles. This rinse mixture is also poured across the sheet filter. Magnetically responsive particles held to the vessel bottom by the magnetic field are mobilized in a solvent upon removal of the vessel from the magnetic field. This mixture of solvent and magnetically responsive particles is poured across a second filter to isolate the magnetic particles independently of the non-magnetic particles for separate analysis.

18 Claims, 2 Drawing Sheets

METHOD AND APPARATUS FOR AIDING MACHINE OIL ANALYSIS

BACKGROUND OF THE INVENTION

The present invention relates to methods and apparatus for analyzing machine lubrication oil.

Lubrication oil circulated through the bearings, pins and sliders of an operating machine both effects and reflects the machine condition. By the size, shape, density and magnetic responsiveness of particles suspended or mixed within the lubrication oil, substantial conclusions may be drawn or inferred about the state of machine wear, the rate of such wear and in some cases, the identity of the particular component yielding such wear or degradation.

Although it is known to magnetically separate iron wear particles from a machine lube oil sample, the viscosity of such oil is usually sufficiently high to retard separation even in the presence of a magnetic field. Extremely small, non-magnetic metal particles such as brass, copper and aluminum are extremely slow to settle under gravity forces alone. Low density non-magnetic particles such as soot and silica may remain buoyantly suspended.

It is also known to separate such particles by diluting an oil sample with solvent to lower the viscosity and then filter separating suspended particles from the diluted sample. However, this procedure leaves all the separated particles in a consolidated mass on or in the filter medium subject to limited analysis.

It is an object of the present invention, therefore, to provide a process and apparatus for separating magnetically responsive particles from a machine lubrication oil independently of non-magnetic particles.

Another object of the present invention is a small, portable apparatus for effectively separating magnetic particles from an oil sample and from other, non-magnetic, particles.

A still further object of the present invention is to provide a rapid and highly accurate field analysis method for machine lubrication oil.

SUMMARY OF THE INVENTION

These and other objects of the present invention are accomplished by a preferred embodiment of the invention which includes a portable, hand-held apparatus that confines an oil sample holding vessel within a receptacle pocket. The apparatus includes a rechargeable battery driven oscillation mechanism for vibrating the sample vessel at a controlled frequency and amplitude and for a controlled interval. Simultaneous with the vibration, the sample vessel is subjected to a magnetic field oriented to bias magnetically responsive particles toward the bottom of the sample vessel.

At the end of the controlled vibratory period, the oil sample is poured from the vessel while remaining in the vibrator pocket and within the magnetic field thereby holding those magnetically responsive particles attracted to the vessel bottom in place. When poured from the sample vessel, the liquid decantate is poured through a filter to screen remaining, non-magnetic particles above a predetermined filter minimum particle size.

Still in the vibrator pocket, solvent is poured into the sample vessel and swirled to mobilize non-magnetic residuals on the vessel bottom and decanted through the aforesaid filter.

The aforesaid procedure quickly and effectively separates magnetic particles in the lubrication system from non-magnetic materials such as non-ferrous metals and silica. When filter paper sheets are used, the non-magnetic material may be conveniently exposed for visual analysis. Similarly, the magnetic material may be deposited on a separate filter paper or screen by removing the sample vessel from vibrator pocket, mobilizing the magnetic material on the bottom thereof with solvent and pouring the mixture across the separate filter medium.

In another embodiment of the invention, the sample vessel is removably combined with the magnet as a unit that is selectively detached from the vibration unit. This configuration of the invention allows the sample to be handled in the presence of the magnetic field but independent of the vibration generator, its energy source or other analysis accessories that may be unified with the invention apparatus.

DESCRIPTION OF THE DRAWINGS

The foregoing features and characteristics of the invention will be more readily understood from the following description when considered in conjunction with the accompanying drawings in which.

DESCRIPTION OF THE PREFERRED EMBODIMENTS

Figure 1:
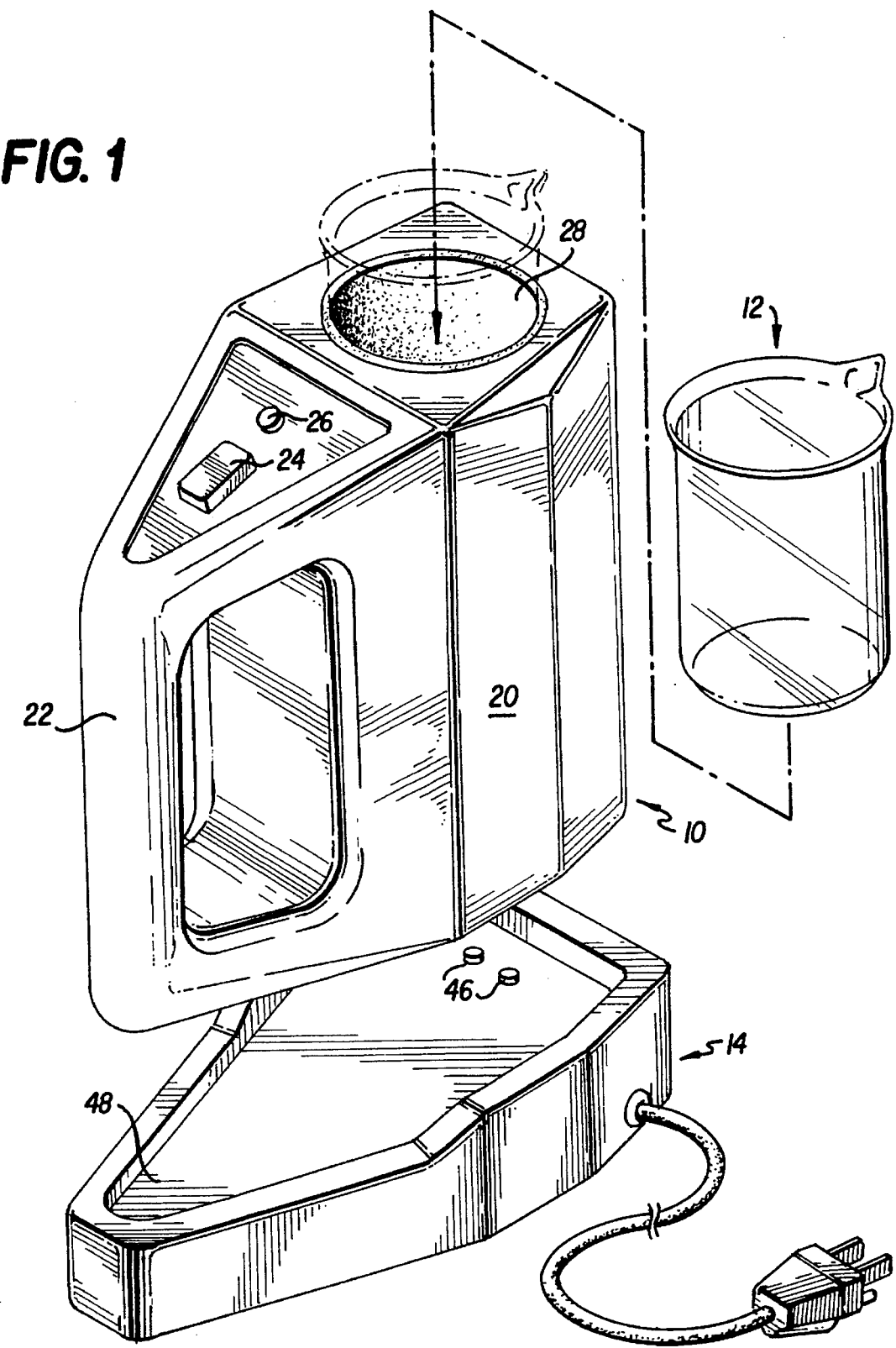
FIG. 1 is a pictorial view of the vibratory apparatus and sample vessel.

Relative to the drawing wherein like reference characters designate like or similar elements in the two figures, the FIG. 1 pictorial illustrates the three major components of the invention comprising the vibratory holder unit 10, the sample vessel 12 and the recharging base 14.

Constituent elements of the vibratory unit 10 comprise an outer case 20 having an integrally molded handle 22. In an upper face portion of the handle 22 is an operating switch 24. If desired, an operational status lamp 26 may also be provided.

From the upper end of the main body of the vibratory unit 10 is a substantially cylindrical receptacle pocket 28. The pocket 28 is lined with felt, rigid plastic foam or other compliant, frictional material 30 to hold the vessel 12 in the pocket 28 when the holder unit 10 and vessel 12 are inverted to pour out liquid vessel contents.

Figure 2:
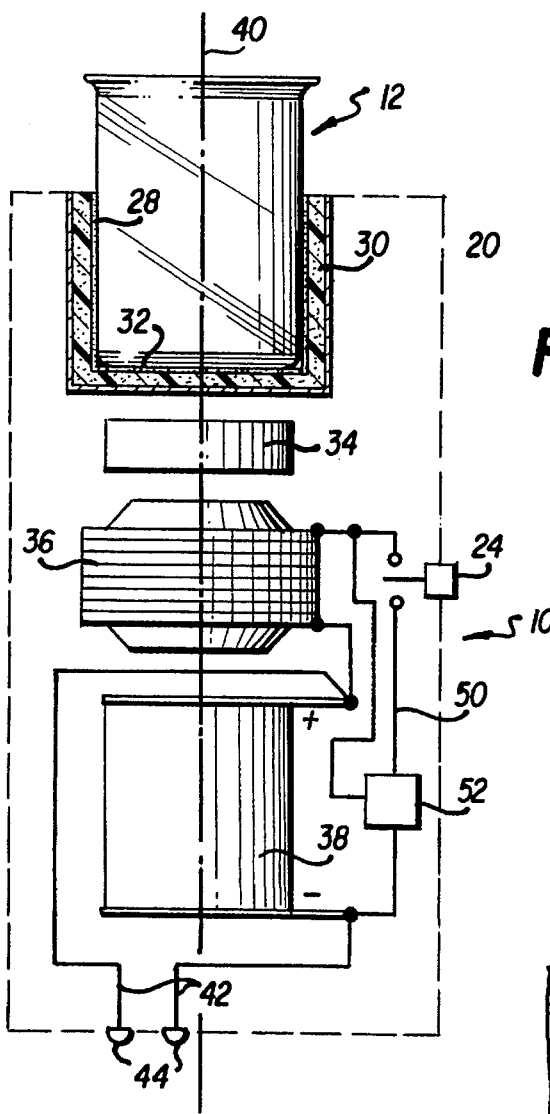
FIG. 2 is a schematic of the vibratory apparatus construction as assembly elements.

With respect to FIG. 2, a disk shaped permanent magnet 34 is secured to the casement body 20 in coaxial alignment with the pocket axis 40 whereby the magnet flux field along the disk cylinder axis is coincident with the pocket axis 40 and oriented to bias magnetically responsive particles within the pocket volume toward the pocket bottom 32, which is the interior termination plane of the pocket cylinder 28. For a preferred embodiment of the invention configured to a 100 ml glass laboratory beaker vessel 12, a nickel plated, grade 35, deodymium iron-boron permanent field disc magnet of 25 mm diameter and 7 mm deep was selected.

Also secured to the casement 20 in alignment with the pocket axis 40 is a rotating eccentric vibration generator 36. The preferred vibrational frequency range is about 120 to 150 Hz and particularly, about 139 Hz. The dominant vibratory plane is radial i.e. transverse to the pocket axis 40 with an acceleration rate of about 0.5 g. In directions parallel with the axis 40, the generator provides an acceleration rate of about 0.06 g.

Although a rotating eccentric is the preferred vibrational mechanism, it will be understood by those in the art that other mechanisms such as oscillating magnet cores may also be used with some modification.

Energizing the vibration generator 36 is a rechargeable battery unit 38. Circuitry 42 including pins 44 connect with pins 46 in the charging base 14 to recharge the battery unit 38 when the vibratory holder unit 10 is socketed in the base receptacle 48.

A timer 52 in the operating switch circuit 50 provides a predetermined operating interval: 40 seconds, for example.

In use, a 50 to 75 ml machine oil sample is placed in the vessel 12 and socketed into the pocket 28 of the vibratory holder unit 10. Switch 24 is momentarily closed to initiate current flow through the timer 52 for driving the vibration generator 36. The flux field of magnet 34, standing permanently in the spacial volume of pocket 26, simultaneously biases magnetically responsive material such as iron particles suspended in the oil sample toward the vessel bottom 32. The vibration greatly accelerates the particle movement through the viscous liquid under the magnetic field bias.

Following the desired vibratory interval, the oil in the vessel 10 is poured across a suitable planar filter element such as a 500 micron filter sheet to consolidate the non-magnetic particle constituency of the sample. Such decanting is done while the vessel 12 remains in the pocket 28 of the vibratory holder unit.

Preferably, the vessel 12 is rinsed a first time with a solvent which is also poured over the non-magnetic material filter while the vessel 12 remains in the pocket 28.

A second solvent rinsing of the vessel 12 is performed with the vessel removed from the pocket 28 to mobilize the magnetic material heretofore held to the vessel bottom. This mixture of solvent and magnetic material is poured across a second 500 micron sheet filter to consolidate the magnetic material.

Consolidated on respective filter elements, the two particle groups may now be visually analyzed separately with non-ferrous particles not being subject to confusion with ferrous particles and vice-versa.

Figure 3:
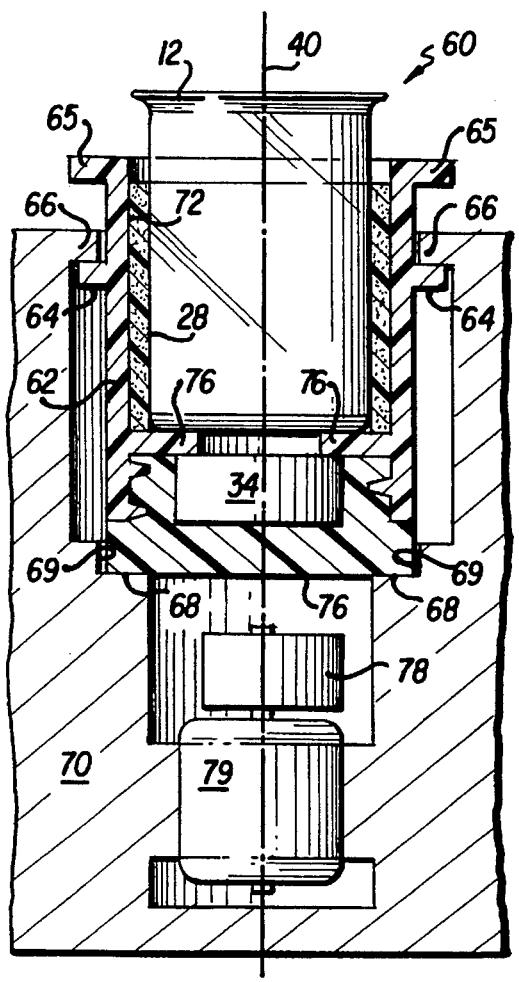
FIG. 3 schematically illustrates an alternate embodiment of the invention.

The alternate embodiment of FIG. 3 is designed to be integrated into a larger base that would be impractical for manual inversion. In this embodiment, the beaker 12 and magnet 34 are independent constituents of a separable unit 60. The vessel 12 pocket of this embodiment is a cylindrical plastic housing 62 having lugs 64 that engage the underside of frame lugs 66 with a twist to advance the interior end of the unit 60 against a base edge surface 68 of the frame 70 surrounded by a socket wall 69. A knurled grip ridge 65 surrounds the upper rim of the cylindrical housing to facilitate manual twisting of the unit and meshing of the lugs 64 and 66.

As in the first embodiment, the internal bore wall 72 of the cylindrical housing 62 is lined with a compliant frictional material 74 such as felt or rigid plastic foam. A floor ridge 76 forms a bottom to the cylindrical pocket for limiting the depth to which the beaker 12 may be inserted.

This FIG. 3 embodiment orients the flux field of magnet 34 coaxially with the sample vessel axis 40 by adhesively securing the magnet disc within an externally threaded plastic plug 76.

Rotational disengagement of the lugs 64 and 66 will permit the unit 60 to be axially removed from the frame 70 wherein the rotating eccentric 78 and motor drive 79 are secured. Energy to drive the motor 79 may be derived from battery sources as described for the FIG. 1 and 2 embodiments or from the commercial distribution alternating current grid.

When separated from the frame 70, the sample within beaker 12 is still within the flux field of magnet 34 to hold iron particles attracted to the beaker 12 bottom in place as the sample oil is poured off. Later, when it is desired to remove the segregated iron particles from the beaker 12, the beaker may be withdrawn from the cylinder pocket 28 or the magnet bearing plug 76 unscrewed from the cylinder housing 62.

A third, non-illustrated embodiment of the invention may comprise the combination of a vibrational unit with oil analysis apparatus described by U.S. Pat. No. 5,262,732 to A.D. Dickert et al. According to the disclosure of that patent, an oil sample is placed in a screw top vessel which is sealed with a cap having an integrated dielectric sensor. The capped vessel is inverted to flood the plate elements of the sensor with the oil sample and the sensory cap is connected to appropriately calibrated, electric property sensory, instrumentation. Beneath the electrically connected, dielectric sensing cap is a permanent magnet to attract magnetic material onto the sensor surface. Modified pursuant to the present invention, a vibration generator as described relative to FIGS. 1, 2 or 3 herein is secured along the vessel and magnet axis beneath the magnet for acceleration of magnetic particle deposition. In all other respects, the Dickert et al analysis proceeds as disclosed in that patent.

In the context of the present invention nomenclature, the inverted sample bottle of Dickert et al would directly correspond to the sample pocket of FIGS. 1, 2 and 3 herein by confining the tested oil sample with an oriented magnetic flux field while the sample is simultaneously vibrated.

Although the FIG. 1, 2 and 3 embodiments of the invention are most suitably adapted to the preparation of oil samples for visual analysis by manual filtration, it will also be understood that the Dickert et al disclosure evaluates a sample by electrochemical analysis. Correspondingly, the vibrator stimulated, magnetic sample preparation procedure of the present invention may be adapted to many automated analysis procedures with selected sensors responsive to electrochemical, electrooptical and electromagnetic analysis.

Having fully disclosed the preferred embodiment of our invention,

We claim:

1. An apparatus for preparing a sample of machine lubrication oil for analysis comprising:

a tool body having an assembly axis;

a receptacle pocket in said body for positionally securing a removable sample vessel along said axis to confined static volume of fluid therein;

a magnetic field source proximately of said pocket and oriented with respect to said axis to bias magnetically responsive material in said sample toward one end of said pocket; and, a vibration generator in said body to vibrate a fluid sample in said pocket.

2. An apparatus as described by claim 1 further comprising a storage battery energy source for said vibration generator.

3. An apparatus as described by claim 2 wherein said storage battery energy source is rechargeable.

4. An apparatus as described by claim 1 wherein said receptacle pocket is a substantially cylindrical recess in said tool body having a cylindrical axis substantially coinciding with said assembly axis.

5. An apparatus as described by claim 4 wherein receptacle pocket wall surfaces are provided with a compliant frictional material for securing the position of a fluid sample holding vessel.

6. An apparatus as described by claim 5 wherein a permanent magnet is positioned within said tool body along said assembly axis proximate of an interior termination plane for said cylindrical recess.

7. An apparatus as described by claim 1 wherein said vibration generator comprises a rotatively driven mass.

8. An apparatus as described by claim 1 wherein said vibration generator comprises a rotatively driven eccentric.

9. An apparatus as described by claim 1 wherein said vibration generator comprises a vibrating magnet core.

10. An apparatus as described by claim 1 wherein said vibration generator vibrates at a rate of 140 to 150 Hz.

11. An apparatus as described by claim 1 wherein said vibration generator accelerates at the rate of approximately 0.5 g in directions substantially radially of said axis.

12. An apparatus as described by claim 11 wherein said vibration generator accelerates at the rate of approximately 0.06 g in directions substantially parallel with said axis.

13. A method of preparing a sample of machine lubrication oil for analysis, said method comprising the steps of:

placing a representative, static volume sample of oil in a non-metallic vessel;

securing said vessel held sample within an axially aligned magnetic flux field, said vessel being aligned within said flux field to bias magnetically responsive particles mixed within said sample toward a bottom surface of said vessel; and, vibrating said vessel held sample at an oscillation rate of approximately 120 to 150 Hz, to accelerate migration of said magnetic particles to said vessel bottom surface.

14. A method of preparing a sample of machine oil for analysis as described by claim 13 wherein said sample is vibrationally accelerated in directions transverse to said flux field axis about 0.5 g.

15. A method of preparing a sample of machine oil for analysis as described by claim 14 wherein said sample is vibrationally accelerated additionally in directions parallel with said flux field axis at about 0.06 g.

16. A method of preparing a sample of machine oil for analysis as described by claim 13 wherein liquid constituent is poured from said vessel while said vessel remains in said flux field, said liquid constituent being passed through a first plane surfaced filter element to segregate non-magnetic particles mixed therein for analysis.

17. A method of preparing a sample of machine oil for analysis as described by claim 16 wherein non-magnetic particles remaining in said vessel following separation of said liquid constituent are mobilized by solvent while said vessel remains in said flux field, the solvent and particle mixture being passed through said first plane surfaced filter element for analysis.

18. A method of preparing a sample of machine oil for analysis as described by claim 17 wherein said vessel is removed from said flux field and magnetically responsive particles on said vessel bottom surface are mobilized by solvent, the solvent and particle mixture being passed through a second plane surfaced filter element for analysis.

* * * * *